United States Patent [19]

Evans et al.

[11] Patent Number: 4,644,070

[45] Date of Patent: * Feb. 17, 1987

[54] CHROMAN-3-OL COMPOUNDS

[75] Inventors: John M. Evans, Roydon; Robin E. Buckingham, Welwyn Garden City; Kenneth Willcocks, Harlow, all of England

[73] Assignee: Beecham Group p.l.c., England

[*] Notice: The portion of the term of this patent subsequent to May 1, 2001 has been disclaimed.

[21] Appl. No.: 683,018

[22] Filed: Dec. 18, 1984

Related U.S. Application Data

[62] Division of Ser. No. 482,628, Apr. 6, 1983, Pat. No. 4,542,149.

[30] Foreign Application Priority Data

Apr. 8, 1982 [GB] United Kingdom ................. 8210490

[51] Int. Cl.$^4$ ........................................... C07D 311/68
[52] U.S. Cl. ..................... 549/399; 549/345
[58] Field of Search ............................... 549/399, 345

[56] References Cited

U.S. PATENT DOCUMENTS 4,446,113  5/1984  Evans et al. ..................... 546/196

Primary Examiner—Nicky Chan
Attorney, Agent, or Firm—Jacobs & Jacobs

[57] ABSTRACT

Anti-hypertensive compounds of formula (I):

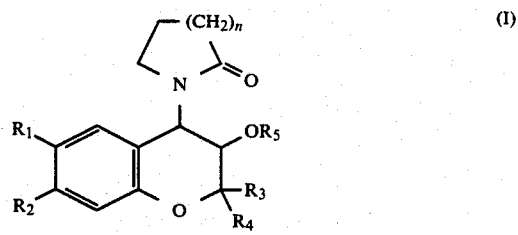

wherein:
one of $R_1$ and $R_2$ is nitro, cyano or $C_{1-3}$ alkylcarbonyl, and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl, or $R_3$ and $R_4$ together with the carbon atom to which they are attached are $C_{3-6}$ spiroalkyl;
$R_5$ is hydrogen, $C_{1-3}$ alkyl or $C_{1-8}$ acyl; and
n is 1 or 2; the lactam group being trans to the $OR_5$ group; or, when the other of $R_1$ and $R_2$ is amino, a pharmaceutically acceptable salt thereof.

3 Claims, No Drawings

CHROMAN-3-OL COMPOUNDS

CROSS-REFERENCE

This is a division of Ser. No. 482,628, filed Apr. 6, 1983, now U.S. Pat. No. 4,542,149.

The present invention relates to novel benzopyrans having pharmacological activity, to processes and intermediates for use in their preparation, to pharmaceutical compositions and their preparation, and to their use in the treatment of mammals.

U.S. Pat. No. 4,110,347 discloses compounds having blood pressure lowering activity which are of formula (A):

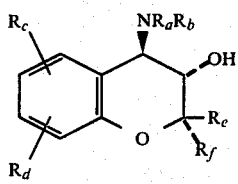

and acid addition salts thereof, wherein $R_a$ is a hydrogen atom or a $C_{1-9}$ hydrocarbon group optionally substituted by a hydroxyl or $C_{1-6}$ alkoxyl group; $R_b$ is a hydrogen atom or $C_{1-6}$ alkyl group, or $NR_aR_b$ is a 3-8 membered heterocyclic group optionally substituted by one or two methyl groups; $R_c$ is a hydrogen or halogen atom or a $C_{1-6}$ alkyl, $C_{2-6}$ alkenyl, $C_{1-6}$ alkoxy, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrile or $AOR_g$, $ASR_g$, $ASO_2R_g$, $ANHR_g$, $ANR_gCOR_h$, $ANR_gSO_2R_h$ or $ANR_gCO_2R_h$ in which A is an alkylene group of 1-4 carbon atoms, $R_g$ is an alkyl group of 1-4 carbon atoms, and $R_h$ is an alkyl group of 1 to 4 carbon atoms; $R_d$ is a hydrogen or halogen atom or methyl or methoxy, or $R_c$ together with $R_d$ forms a —CH=CH—CH=CH—, —NH—CH=CH—, —CH$_2$—CH$_2$—CH$_2$—CH$_2$— or —CH$_2$—CH$_2$—CH$_2$—CO— system; $R_e$ is a hydrogen atom or a $C_{1-6}$ alkyl or phenyl group; and $R_f$ is a hydrogen atom or a $C_{1-6}$ alkyl or phenyl group.

European Patent Publication No. 28449 discloses compounds having blood pressure lowering activity, with low levels of unwanted cardiac effects, which compounds are of formula (B):

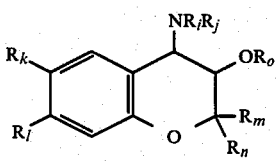

$R_n$ is a hydrogen atom or a lower alkyl group;
$R_m$ is a hydrogen atom or a lower alkyl group;
$R_o$ is a hydrogen atom or a lower alkyl group;
$R_i$ is a hydrogen atom or a lower alkyl group;
$R_j$ is a lower alkyl or a substituted alkyl group;
or $R_i$ and $R_j$ are joined so that together with the nitrogen atom to which they are attached they form a 5-, 6- or 7-membered ring optionally containing an oxygen or sulphur atom;
$R_k$ is an electron withdrawing group;
$R_l$ is an electron donating group; and the $NR_iR_j$ and $OR_o$ moieties are trans.

European patent publication No. 28064 discloses compounds having blood pressure lowering activity, with low levels of unwanted cardiac effects, which compounds are of formula (C):

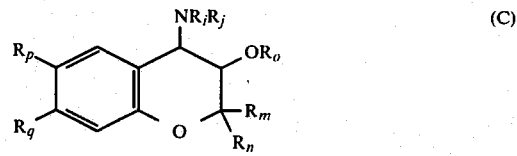

and salts and pro-drugs thereof, wherein:
$R_n$, $R_m$, $R_o$, $R_i$ and $R_j$ are as defined for formula (B), and $R_p$ is an electron donating group and $R_q$ is an electron withdrawing group; and the $NR_iR_j$ and $OR_o$ moieties are trans.

A structurally distinct class of benzopyrans have now been discovered which are characterised by the presence of an oxo group in the nitrogen-containing ring that substitutes the benzopyran in the 4-position and by the presence of a substituent in each of the 6- and 7-positions. Such benzopyrans, moreover, have been found to have blood pressure lowering activity.

Accordingly, the present invention provides a compound of formula (I):

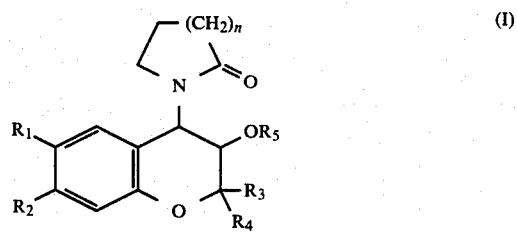

wherein:
one of $R_1$ and $R_2$ is nitro, cyano or $C_{1-3}$ alkylcarbonyl, and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl, or $R_3$ and $R_4$ together with the carbon atom to which they are attached are $C_{3-6}$ spiroalkyl;
$R_5$ is hydrogen, $C_{1-3}$ alkyl or $C_{1-8}$ acyl; and
n is 1 or 2; the lactam group being trans to the $OR_5$ group; or, when the other of $R_1$ and $R_2$ is amino, a pharmaceutically acceptable salt thereof.

Preferably, one of $R_1$ and $R_2$ is nitro or cyano
Preferably, the other of $R_1$ and $R_2$ is amino optionally substituted by one or two $C_{1-6}$ alkyl or by $C_{2-7}$ alkanoyl. In particular, the other of $R_1$ and $R_2$ is amino, methylamino, dimethylamino or acetylamino.

Most preferably, $R_1$ is nitro or cyano and $R_2$ is amino.
Preferably, $R_3$ and $R_4$ are both $C_{1-4}$ alkyl. In particular, they are both methyl or ethyl, preferably both methyl.

When $R_5$ is $C_{1-3}$ alkyl, preferred examples thereof include methyl, ethyl and n-propyl, of which methyl is most preferred. When $R_5$ is $C_{1-8}$ acyl, a preferred class is unsubstituted carboxylic acyl, such as aliphatic acyl or benzoyl. However, $R_5$ is preferably hydrogen.

It is preferred that the compounds of formula (I) are in substantialy pure form.

The present invention extends to the compounds of formula (I) whenever prepared synthetically.

The compounds of formula (I) have assymetric centres and therefore exist in optically active forms. The present invention extends to all such forms individually and to mixtures of them.

Particular examples of compounds of formula (I) include:

6-acetamido-7-nitro-3,4-dihydro-trans-4-(2-ketopyrrolidinyl)-2,2-dimethyl-2H-benzo[b]pyran-3-ol; 6-amino-7-nitro-3,4-dihydro-trans-4-(2-ketopyrrolidinyl)2,2-dimethyl-2H-benzo[b]pyran-3-ol or a pharmaceutically acceptable salt thereof; 6-nitro-7-acetamido-3,4-dihydro-trans-4-(2-ketopyrrolidinyl)-2,2-dimethyl-2H-benzo[b]pyran-3-ol; 6-nitro-7-amino-3,4-dihydro-trans-4-(2-ketopyrrolidinyl)-2,2-dimethyl-2H-benzo[b]pyran-3-ol or a pharmaceutically salt thereof; or 6-cyano-7-amino-3,4-dihydro-trans-4-(2-ketopyrrolidinyl)-2,2-dimethyl-2H-benzo[b]pyran-3-ol or a pharmaceutically acceptable salt thereof.

The present invention also provides a process for preparing a compound of formula (I), which comprises cyclising a compound of formula (II), or a metal salt thereof:

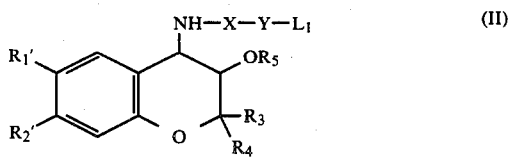

wherein one of $R_1'$ and $R_2'$ is nitro, cyano or $C_{1-3}$ alkylcarbonyl or a group or atom convertible thereto and the other is methoxy or amino optionally substituted by one or two $C_{1-6}$ alkyl or by $C_{2-7}$ alkyl or a group or atom convertible thereto, $R_3$ to $R_5$ are as defined hereinbefore, one of X and Y is CO and the other is $(CH_2)_{n+2}$, n being as hereinbefore defined, $L_1$ is a leaving group, and the substituted amino group is trans to the $OR_5$ group; in the case when one of $R_1'$ and $R_2'$ is a group or atom convertible into nitro, cyano or $C_{1-3}$ alkylcarbonyl, converting the group or atom into nitro, cyano or $C_{1-3}$ alkylcarbonyl; in the case when the other of $R_1'$ and $R_2'$ is a group or atom convertible into methoxy or amino optionally substituted by one or two $C_{1-6}$ alkyl or by $C_{2-7}$ alkanoyl, converting the group or atom into methoxy or amino optionally substituted by one or two $C_{1-6}$ alkyl or by $C_{2-7}$ alkanoyl; optionally converting $R_1$ or $R_2$ into another $R_1$ or $R_2$ respectively; in the case when $R_5$ is hydrogen, optionally converting it into $C_{1-3}$ alkyl or $C_{1-8}$ acyl; and, in the case when one of $R_1$ and $R_2$ is amino, optionally forming a pharmaceutically acceptable salt.

Preferably, X is CO and Y is $(CH_2)_{n+2}$, n being as defined hereinbefore.

The leaving group ($L_1$) is a group that is displaceable by a secondary amino nucleophile. When X is CO and Y is $(CH_2)_{n+2}$, a preferred example of such a leaving group is chloro. On the other hand, when X is $(CH_2)_{n+2}$ and Y is CO, examples of such a leaving group include hydroxy and, preferably, $C_{1-4}$ alkoxy, such as ethoxy.

When X is CO and Y is $(CH_2)_{n+2}$, the cyclisation is preferably carried out in a solvent, such as acetone, in the presence of a base, such as potassium carbonate. On the other hand, when X is $(CH_2)_{n+2}$ and Y is CO, the cyclisation is preferably carried out by heating the compound of formula (II) under reflux in an inert solvent, such as xylene or toluene.

When a metal salt of formula (II) is used, the sodium salt is preferred. However, it is even more preferred not to use a metal salt at all, especially as any elimination side reactions are thereby avoided.

Examples of a group or atom convertible into nitro, cyano or $C_{1-3}$ alkylcarbonyl are generally known in the art of aromatic chemistry. For example, a hydrogen atom is convertible into nitro by nitration, an especially useful conversion when the other of $R_1'$ and $R_2'$ is amino substituted by $C_{2-7}$ alkanoyl. Another example is an α-hydroxymethyl group which is convertible into acetyl by oxidation.

Examples of a group or atom convertible into methoxy or amino optionally substituted by one or two $C_{1-6}$ alkyl or by $C_{2-7}$ alkanoyl are also generally known in the art of aromatic chemistry. For example, a hydroxy group is convertible into methoxy by methylation and a halo atom is convertible into amino by amination, an especially useful conversion when one of $R_1'$ and $R_2'$ is cyano.

Examples of optionally converting $R_1$ or $R_2$ into another $R_1$ or $R_2$ respectively include optionally converting amino into amino substituted by one or two $C_{1-6}$ alkyl or by $C_{2-7}$ alkanoyl and optionally converting amino substituted by $C_{2-7}$ alkanoyl into amino.

All such conversions are generally described in the art.

In the case when $R_5$ is hydrogen, the optional conversion of it into $C_{1-3}$ alkyl lis preferably carried out using a $C_{1-3}$ halide, the reation being carried out in an inert solvent, such as toluene, in the presence of a base, such as potassium t-butoxide.

In the case when $R_5$ is hydrogen, the optional conversion of it into $C_{1-8}$ acyl is preferably carried out in an non-hydroxylic solvent in the presence of a condensation-promoting agent, such as dicyclohexylcarbodiimide.

In the case when the other of $R_1$ and $R_2$ is amino, the optional formation of a pharmaceutically acceptable salt may be carried out in accordance with any conventional procedure.

A compound of formula (II), wherein X is CO and Y is $(CH_2)_{n+2}$, may be prepared by reacting a compound of formula (III),

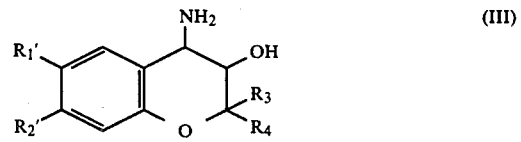

wherein $R_1'$, $R_2'$, $R_3$ and $R_4$ are as definedhereinbefore, and the amino group is trans to the hydroxy group, with a compound of formula (IV),

wherein X, Y and $L_1$ are as defined hereinbefore, and $L_2$ is a leaving group.

The leaving group ($L_2$) is a group that is displaceable by a primary amino nucleophile. Preferred examples of such a group include halo, such as chloro and bromo.

The reaction is preferably carried out in a solvent, such as chloroform or methylene chloride, in the presence of aqueous base, such as aqueous sodium hydroxide.

A compound of formula (III) may be prepared by reacting a compound of formula (V),

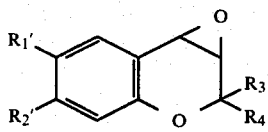

wherein $R_1'$, $R_2'$, $R_3$ and $R_4$ are as hereinbefore defined, with ethanolic ammonium hydroxide solution.

A compound of formula (II), wherein X is $(CH_2)_{n+2}$ and Y is CO, may be prepared by reacting a compound of formula (V), as hereinbefore defined, with a compound of formula (VI), $$H_2N-(CH_2)_{n+2}-COL_1 \qquad (VI)$$

or a salt thereof, wherein n and $L_1$ are as defined hereinbefore.

The reaction between the compounds of formulae (V) and (VI) is preferably carried out in a solvent, such as methanol or ethanol.

When $L_1$ is hydroxy the reaction is preferably carried out in refluxing ethanol in the presence of aqueous sodium bicarbonate. When $L_1$ is $C_{1-4}$ alkoxy, the compound of formula (VI) is preferably in the form of a salt and the reaction is preferably carried out in the presence of sodium hydroxide in ethanol.

Under some conditions, the resulting compound of formula (II) spontaneously cyclises giving a compound of formula (I).

A compound of formula (V) may be prepared, preferably in situ, by reacting a compound of formula (VII):

wherein $R_1'$, $R_2'$, $R_3$ and $R_4$ are as defined hereinbefore and the hydroxy group is trans to the bromo atom, with a base, such as potassium hydroxide, in ether or aqueous dioxan.

Compounds of formula (VII) are known and may be prepared in accordance with any appropriate known process, for example, by the process described in the aforementioned U.S. patents and European patent publications. Schematically, such process can be depicted thus:

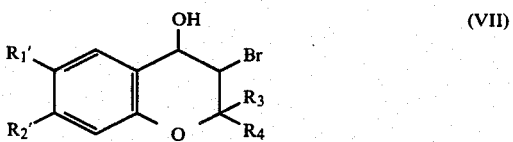

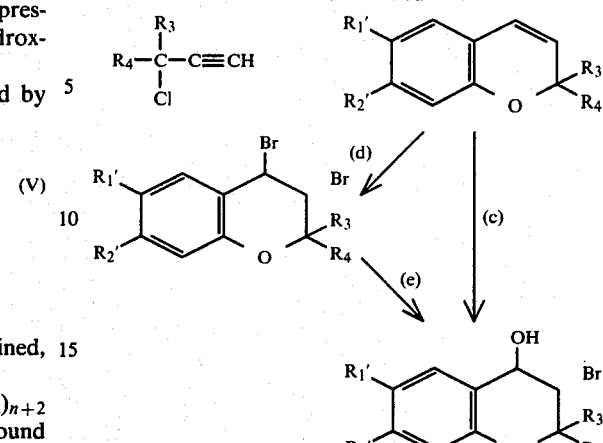

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachoride; and
(e) Acetone/water.

The above process can produce mixtures of compounds during reaction (b) owing to the two sites available for ring formation. It is therefore advisable to remove any of the undesired compound by, for example, chromatography, before reaction (c) or (d).

As mentioned previously, a compound of formula (I) may exist in optically active forms, and the process of the present invention produces mixtures of such forms. The individual isomers may be separated one from the other by chromatography using a chiral phase, such as a chiral carbamate.

It is preferred that a compound of formula (I) is isolated in substantially pure form.

The intermediates of formula (III) are novel and represent part of the patent invention.

The intermediates of formula (IV) and (VI) are known or may be prepared analogously to the preparation of known compounds.

As mentioned previously, the compounds of formula (I) have been found to have blood-pressure lowering activity. They are therefore useful in the treatment of hypertension.

The present invention also provides a pharmaceutical composition, which comprises a compound of the invention and a pharmaceutically acceptable carrier. In particular, the present invention provides an antihypertensive pharmaceutical composition, which comprises an anti-hypertensive effective amount of a compound of the invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and β-blocking agents.

The present invention further provides a compound of the invention for use in the treatment of hypertension.

The present invention yet further provides a method of treating hypertension in a mammal including a human, which comprises administering to the suffering mammal an anti-hypertensive effective amount of a compound of a pharmaceutical composition of the invention.

The following descriptions relate to the preparation of intermediates and the following examples relate to the preparation of a compound of formula (I).

DESCRIPTION 1

Preparation of 6-acetamido-trans-4-amino-3,4-dihydro-2,2-dimethyl-7-nitro-2H-benzo[b]pyran-3-ol

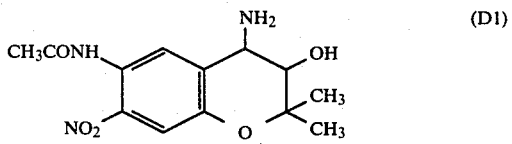

6-Acetamido-3,4-epoxy-3,4-dihydro-2,2-dimethyl-7-nitro-2H-benzo[b]pyran (1.0 g, the preparation of which is described in European Pat. No. 28,064) was dissolved in dry ethanol (150 ml) and saturated with ammonia during 3 h, with cooling. The reaction mixture was stirred at room temperature for 5 days and evaporated. The crude residue was purified on the chromatotron (80% ethyl acetate-pentane to 20% methanol-ethyl acetate gradient elution), to give the title compound (410 mgm). A small portion was converted to the hydrochloride salt and recrystallised from ethanol-diethyl ether, with m.p. 258°–261° C.

Anal. Calc. for $C_{13}H_{18}N_3O_5Cl$: C, 47.0; H, 5.47; N, 12.66; Cl, 10.72. Found: C, 46,92; H, 5.58; N, 12,19; Cl, 10.74%.

DESCRIPTION 2

Preparation of 6-acetamido-trans-4-(4-chlorobutyrylamino)-3,4-dihydro-2,2-dimethyl-7-nitro-2H-benzo[b]pyran-3-ol

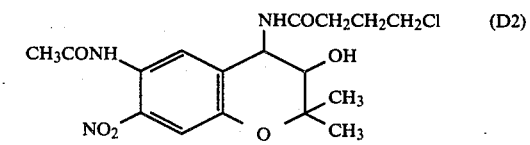

The amino alcohol of Description 1 (300 mgm) and sodium hydroxide pellets (40 mgm) were stirred in chloroform (5 ml) and water (5 ml). Chlorobutyryl chloride (0.12 ml) was added and the reaction mixture stirred for a further 0.5 h. Separation of the layer was followed by extraction of the aqueous layer by chloroform. The combined chloroform extracts were washed with water and brine and dried over anhydrous magnesium sulphate. Filtration and evaporation gave the title compound as a yellow solid (310 mgm). A small portion was recrystallised from pentane-ethyl acetate as yellow crystals of m.p. 178°–180° C.

Anal. Calc. for $C_{17}H_{22}N_3O_6Cl$: C, 51.07; H, 5.55; N, 10.51; Cl, 8.87. Found: C, 50.51; H, 5.41; N, 9.12; Cl, 8.73%.

DESCRIPTION 3

Preparation of 7-acetamido-trans-4-amino-3,4-dihydro-2,2-dimethyl-6-nitro-2H-benzo[b]pyran-3-ol

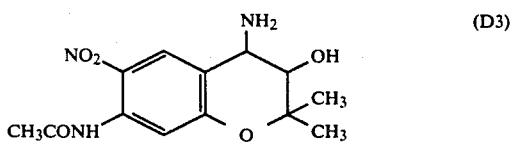

7-Acetamido-3,4-epoxy-3,4-dihydro-2,2-dimethyl-6-nitro-2H-benzo[b]pyran (0.76 g, prepared as in European Pat. No. 28,449) was dissolved in dry ethanol and saturated with dry ammonia, and stirred at room temperature for 21 hr. Evaporation gave a crude mixture which was purified on the chromatotron (using pentane-ethyl acetate in a gradient elution), to give the title compound (280 mg).

DESCRIPTION 4

Preparation of 7-acetamido-trans-4-(4-chlorobutyrylamino)-3,4-dihydro-2,2-dimethyl-6-nitro-2H-benzo[b]pyran-3-ol

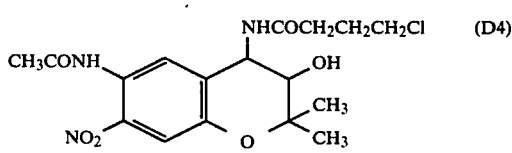

The amino alcohol of Description 3 (190 mg), and sodium hydroxide pellets (26 mg) were stirred in a mixture of chloroform (10 ml) and water (3.2 ml). Chlorobutyryl chloride (91 mg) was added and the reaction mixture stirred for 0.5 h. Separation of the layers and further extraction of the aqueous layer with chloroform, and combination of the chloroform extracts was followed by drying over anhydrous magnesium sulphate. Filtration and evaporation gave the title compound as a yellow solid (210 mg).

Mass spectrum (electron impact) $M^+-H_2O$ at 381.1091. Calc. for $C_{17}H_{20}N_3O_5Cl$ 381.1091.

EXAMPLE 1

Preparation of 6-acetamido-3,4-dihydro-trans-4-(2-ketopyrrolidinyl)-2,2-dimethyl-7-nitro-2-H-benzo[b]pyran-3-ol

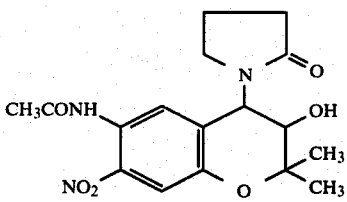
(E1)

The compound of Description 2 (250 mg), potassium carbonate (2 g, anhydrous) and potassium iodide (200 mg) were stirred and heated under reflux in acetone (60 ml) in a nitrogen atmosphere for 18 hr. After cooling, the reaction mixture was filtered and evaporated, and purified on the chromatotron (ethyl acetate with gradual addition of methanol to 20%). The crude product (120 mg) was recrystallised from ethyl acetate as yellow crystals of m.p. 240°-241° C.

Anal. Calc. for $C_{17}H_{21}N_3O_6$: C, 56.20; H, 5.83; N, 11.56. Found: C, 55.77; H, 5.69; N, 11.45%.

EXAMPLE 2

Preparation of 6-amino-3,4-dihydro-trans-4-(2-ketopyrrolidinyl)-2,2-dimethyl-7-nitro-2H-benzo[b]pyran-3-ol

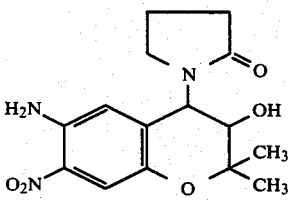
(E2)

The compound of Example 1 (130 mg), 5N HCl (5 ml) and ethanol (9 ml) were heated under reflux for 3 h. After cooling, the reaction mixture was diluted with water and basified with dilute sodium hydroxide solution, extracted with ethyl acetate, and dried with anhydrous magnesium sulphate. Removal of drying agent and evaporation gave a red solid (130 mg). Recrystallisation from ethyl acetate-pentane gave the nitroamine (40 mg) as brick red crystals of m.p. 244°-245° C.

Anal. Calc. for $C_{15}H_{19}N_3O_5$: C, 56.07; H, 5.96; N, 13.07. Found: C, 56.37; H, 6.29; N, 12.14%.

Mass spectrum (electron impact) M+ at M/Z 321.1330. Calc. for $C_{15}H_{19}N_3O_5$ 321.1325.

EXAMPLE 3

Preparation of 7-acetamido-3,4-dihydro-trans-4-(2-ketopyrrolidinyl)-2,2-dimethyl-6-nitro-2H-benzo[b]pyran-3-ol

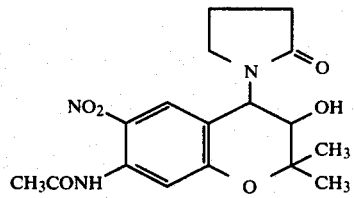
(E3)

The compound of Description 4 (220 mg), potassium carbonate (1.76 g anhydrous) and potassium iodide (180 mg) were stirred in acetone (53 ml) and heated to reflux temperature under nitrogen for 8 hr. After cooling, filtration and evaporation, the crude residue was recrystallised from ethanol to give the title compound (50 mg) as yellow crystals of m.p. 266°-268° C.

Mass spectrum (electron impact) M+ at m/z 363.1435 Calc. for $C_{17}H_{21}N_3O_6$ 363.1430.

EXAMPLE 4

Preparation of 6 nitro-7-amino-3,4-dihydro-trans-4-(2-keton-pyrrolidinyl)-2,2-dimethyl-2H-benzo[b]pyran-3-ol

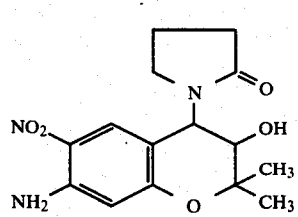
(E4)

The title compound was prepared by hydrolysis of the compound of Example 3 using the same procedure as described in Example 2., m.p. 310°-313° C. (recrystallised from ethanol).

PHARMACOLOGICAL DATA

Systolic blood pressures were recorded by a modification of the tail cuff method described by I. M. Claxton, M. G. Palfreyman, R. H. Poyser, R. L. Whiting, European Journal of Pharmacology, 37, 179 (1976). W+W BP recorder, model 8005, was used to display pulses prior to all measurements rats were placed in a heated environment (33.5+0.5° C.) before transfer to a restraining cage. Each determination of blood pressure was the mean of at least 6 readings. Spontaneously hypertensive rats (ages 12-18 weeks) with systolic blood pressures >170 mmHg were considered hypertensive.

| Compound | Time Post Dose Hours | % Change in Systolic Blood | % Change in Heart Rate |
|---|---|---|---|
| Example 1 | | | |
| 6 rats | | | |
| Dose 3 mg/kg | 1 | −14 ± 3 | −5 ± 1 |
| p.o | 2 | −11 ± 4 | −8 ± 3 |
| Initial Blood | 4 | −8 ± 3 | −11 ± 2 |
| Pressure | | | |
| 215 ± 4 mmHg | 6 | −22* | −8 |
| Initial Heart | 24 | −7 ± 5 | −11 ± 4 |

| Compound | Time Post Dose Hours | % Change in Systolic Blood | % Change in Heart Rate |
|---|---|---|---|
| Rate | | | |
| 514 ± 9 beats/ | | | |
| min | | | |
| *at 6 hours 4 rats had no measurable pulse | | | |
| Example 2 | | | |
| 6 rats | | | |
| Dose 1 mg/kg | 1 | −14 ± 4 | +1 ± 2 |
| p.o | 2 | −8 ± 5 | −2 ± 2 |
| Initial Blood | 4 | * | |
| Pressure | | | |
| 215 ± 8 mmHg | 6 | −25 ± 6** | −10 ± 1 |
| Initial Heart | 24 | −8 ± 6 | −24 ± 2 |
| Rate | | | |
| 512 ± 11 beats/ | | | |
| min | | | |
| *at 4 hours all six rats had no measurable pulse | | | |
| **at 6 hours 3 rats had no measurable pulse | | | |
| Example 3 | | | |
| 5 rats | | | |
| Dose 1 mg/kg | 1 | −60 ± 4* | −5 ± 3 |
| p.o | 2 | −56** | −12 |
| Initial Blood | 4 | *** | |
| Pressure | | | |
| 203 ± 5 mmHg | 6 | −51**** | −3 |
| Initial Heart | 24 | +1 ± 2 | −6 ± 5 |
| Rate | | | |
| 491 ± 8 beats/ | | | |
| min | | | |
| *At 1 hour 2 rats had no measurable pulse | | | |
| **At 2 hours 3 rats had no measurable pulse | | | |
| ***At 4 hours all 5 rats had no measurable pulse | | | |
| ****At 6 hours 4 rats had no measurable pulse | | | |
| Example 4 | | | |
| 6 rats | | | |
| Dose 0.3 mg/kg | 1 | −66 ± 1* | 1 ± 5 |
| p.o | 2 | −68** | −2 |
| Initial Blood | 4 | −51*** | +4 |
| Pressure | | | |
| 206 ± 6 mmHg | 6 | **** | |
| Initial Heart | 24 | | |
| Rate | | | |
| 483 ± 10 beats/ | | | |
| min | | | |

*At 1 hour 2 rats had no measurable pulse
**At 2 hours 4 rats had no measurable pulse
***At 4 hours 5 rats had no measurable pulse
****At 6 hours all rats had no measurable pulse

What we claim is:
1. A compound of the formula:

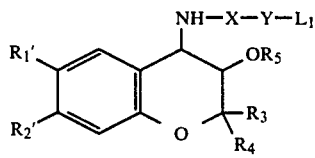

wherein:
one of $R_1'$ and $R_2'$ is nitro, cyano, $C_{1-3}$ alkylcarbonyl, hydrogen or α-hydroxymethyl, and the other is methoxy, amino optionally substituted by one of two $C_{1-6}$ alkyl or by $C_{2-7}$ alkanoyl, or hydroxy or halo;
one of $R_3$ and $R_4$ is hydrogen or $C_{1-4}$ alkyl and the other is $C_{1-4}$ alkyl, or $R_3$ and $R_4$ together with the carbon atom to which they are attached are $C_{3-6}$ spiroalkyl;
$R_5$ is hydrogen, $C_{1-3}$ alkyl or $C_{1-8}$ alkanoyl or benzoyl;
one of X and Y is CO and the other is $(CH)_{n+2}$;
n is 1 or 2;
$L_1$ is chloro when X is CO and is hydroxy or $C_{1-4}$ alkoxy when Y is CO; and
the substituted amino group is trans to the $OR_5$ group.
2. The compound according to claim 1, wherein X is CO, Y is $(CH_2)_{n+2}$ and $L_1$ is chloro.
3. The compound according to claim 1, wherein X is $(CH_2)_{n+2}$, Y is CO and $L_1$ is hydroxy or $C_{1-4}$ alkoxy.

* * * * *